United States Patent [19]

Chase

[11] 4,306,151

[45] Dec. 15, 1981

[54] METHOD OF MEASURING THE AMOUNT OF SUBSTANCE ASSOCIATED WITH A MATERIAL IN THE PRESENCE OF A CONTAMINANT

[75] Inventor: Lee M. Chase, Los Gatos, Calif.

[73] Assignee: Measurex Corporation, Cupertino, Calif.

[21] Appl. No.: 34,199

[22] Filed: Apr. 27, 1979

Related U.S. Application Data

[63] Continuation-in-part of Ser. No. 874,777, Feb. 3, 1978, abandoned.

[51] Int. Cl.³ .......................... G01J 1/00; G01N 23/00
[52] U.S. Cl. ..................................... 250/341; 250/359
[58] Field of Search ............... 250/339, 341, 343, 358, 250/359, 360

[56] References Cited

U.S. PATENT DOCUMENTS

| | | | |
|---|---|---|---|
| 3,641,349 | 2/1972 | Dahlin ................................. | 250/339 |
| 3,675,019 | 7/1972 | Hill et al. ........................... | 250/339 |
| 3,793,524 | 2/1974 | Howarth ............................. | 250/339 |
| 3,870,884 | 3/1975 | Williams ............................. | 250/339 |

FOREIGN PATENT DOCUMENTS 1138711 1/1969 United Kingdom .

*Primary Examiner*—Alfred E. Smith
*Assistant Examiner*—Janice A. Howell
*Attorney, Agent, or Firm*—Ronald Yin; Hal J. Bohner

[57] ABSTRACT

A method of measuring the amount of substance associated with a material in the presence of a contaminant comprises choosing a first band of radiation which lies outside the absorption band of the substance but within the absorption band of the contaminant. The first band is directed at the material; a first detector is positioned to receive the radiation after impinging the material. The first detector converts the radiation received into a first electrical signal. A second band of radiation, which is chosen to lie within the absorption band of the substance, is also within an absorption band of the contaminant. The second band is directed at the material; a second detector is positioned to receive the radiation after impinging the material. The second detector produces a second electrical signal in response to the radiation received. The second electrical signal is subtracted from the first electrical signal.

8 Claims, 2 Drawing Figures

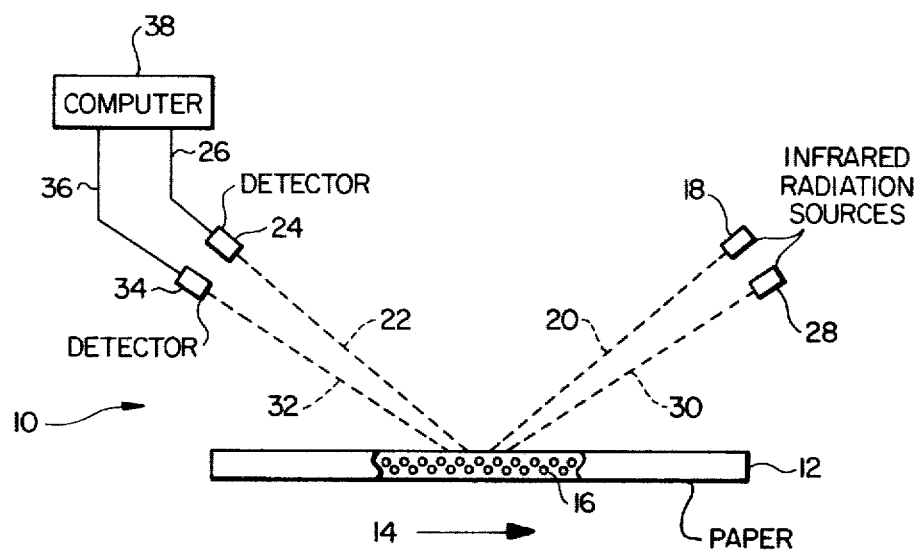
*FIG__1*
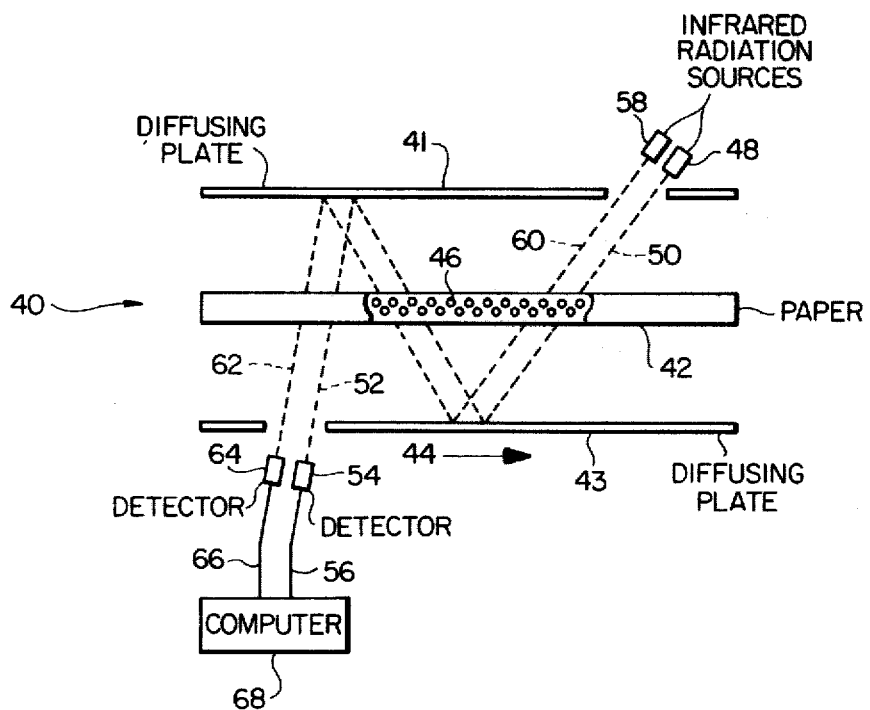
*FIG__2*

METHOD OF MEASURING THE AMOUNT OF SUBSTANCE ASSOCIATED WITH A MATERIAL IN THE PRESENCE OF A CONTAMINANT

This application is a continuation-in-part of a copending application, Ser. No. 874,777, filed on Feb. 3, 1978, by the present inventor and assigned to the same assignee, now abandoned.

BACKGROUND OF THE INVENTION

The present invention relates to a method for measuring the amount of substance associated with a material in the presence of a contaminant, and more particularly to a method for measuring the amount of water associated with a paper material in the presence of carbon.

Methods for detecting moisture in paper material are well known in the prior art, see e.g., U.S. Pat. No. 3,614,450. Typically, an infrared source emits two bands of electromagnetic radiation. A first band (usually 1.8 microns—so called reference channel) is insensitive to absorption by the moisture. A second band (usually 1.94 microns—so called measure channel) is sensitive to absorption by the moisture. The two bands of radiation are directed at the paper material. Detectors are positioned to receive the bands of radiation after they have been reflected from the paper or transmitted through the paper. The detectors convert the radiation received into electrical signals. The ratio of the signal of the reference channel to the measure channel is indicative of the moisture content of the paper material. A fundamental assumption of this method is that neither the reference channel nor the measure channel is sensitive to absorption by other compounds in the paper material.

As ecological demands increase, the use of recycled paper also increases. This has occurred most frequently in the news print industry. Used newspaper is recycled with new pulp to produce fresh news print. The use of recycled news print in the manufacturing process introduces contaminant, namely carbon from the printing ink, into the process. The presence of carbon affects the measurement of moisture of the paper material in that the bands (both reference channel and measure channel) of electromagnetic radiation are absorbed by the carbon. Thus, the ratio of the signals of the reference channel to the measure channel would not be determinitive of the moisture content of the paper material.

Heretofore, one way to correct for the presence of carbon is to determine a priori the influence of carbon on the ratio of the signals for a particular moisture level. For example, at 7% level of moisture for a particular paper material, a ratio of the signals without carbon was determined to be 2.2 and as carbon was introduced the ratio of the signals detected, for the same level of moisture, became 2.0.

For a different level of moisture, the ratio of the signals would also vary as the amount of carbon present in the paper material. In this manner, a family of curves was pre-determined and usually stored in a computer. The amount of carbon present in the paper material was determined from the change in the signal strength of the reference channel. Since the reference channel was insensitive to the presence of water, the change in signal strength of the reference channel could be attributed to the presence of carbon. With knowledge of the ratio of the signals and the amount of deviation of the signal strength in the reference channel, indicating the amount of carbon present, the moisture level of the paper material could thus be calculated from the family of predetermined curves. The drawback of this method, of course, is that a large amount of data had to be predetermined and stored in a medium which is easily and quickly accessible. Moreover, the method that was developed was based upon empirical results and not upon theoretical basis. As a result, it was limited in its accuracy and in its range of application.

SUMMARY OF THE INVENTION

A method of measuring the amount of substance associated with a material in the presence of a contaminant, wherein the contaminant has an electromagnetic radiation absorption characteristic different from the electromagnetic radiation absorption characteristic of the substance, comprises emitting a first band of electromagnetic radiation. The first band is directed at the material and is characterized in that it lies outside an absorption band of the substance but within an absorption band of the contaminant. The first band is detected, after it has impinged on the material, by a detector which produces a first electrical signal in response to the radiation detected. A second band of electromagnetic radiation is also emitted and is aligned to impinge the material. The second band is characterized in that it lies within an absorption band of the substance and also lies within an absorption band of the contaminant. The second band is detected, after it has impinged the material, by a receiver which generates a second electrical signal, in response to the radiation detected. The second electrical signal is subtracted from the first electrical signal.

BRIEF DESCRIPTION OF THE DRAWINGS

FIG. 1 is a schematic side view of an apparatus using the method of the present invention.

FIG. 2 is a schematic side view of another apparatus using the method of the present invention.

DETAILED DESCRIPTION OF THE DRAWINGS

The present invention relates to a method of measuring the amount of substance associated with a material, in the presence of a contaminant. The contaminant has an electromagnetic radiation absorption characteristic different from that of the substance. In the method of the present invention, a first band of electromagnetic radiation is emitted from a source. The first band has the characteristic of being within an absorption band of the contaminant, but outside an absorption band of the substance. The first band is directed to impinge the material. A detector is positioned to receive the first band after impinging the material. A first electrical signal in response to the first radiation detected is generated by the detector. A second band of electromagnetic radiation is produced and is also aligned to impinge the material. The second band has the characteristic of being within an absorption band of the substance and within an absorption band of the contaminant. The second band is detected by a receiver after the second band has impinged the material. The receiver generates a second electrical signal in response to the second band of radiation detected. The second electrical signal is subtracted from the first electrical signal.

A particular application of the method of the present invention is in the measurement of moisture of paper material in the presence of carbon. This can be best understood by referring to FIG. 1, which is a schematic side view of an apparatus 10 using the method of the present invention. A paper material 12, substantially in a sheet form, moves in a direction shown by arrow 14. The paper material 12 can be the manufactured product of a Fourdrinier machine (not shown). As is well known in paper making technology, the control of the amount of moisture or water in the paper is critical in controlling quality and economic return. In the paper material 12 of FIG. 1, however, the paper material 12 also contains carbon particles 16 (greatly exaggerated). A first source 18 emits a first band of electromagnetic radiation, directed towards the paper material 12 in a direction along the dotted line 20. The first band, after impinging the paper material 12 reflects from it and travels in the direction along the dotted line 22 and is received by a first receiver 24. The first receiver 24 converts the first band received into a first electrical signal 26. The first band is chosen such that it lies within an electromagnetic absorption band of carbon but lies outside of an electromagnetic absorption band of water. Typically, this is at about 1.8 microns. A second source 28 emits a second band of electromagnetic radiation, directed towards the paper material 12 in a direction along the dotted line 30. The second band, after impinging the paper material 12, reflects from it and travels in the direction along the dotted line 32 and is received by a second receiver 34. The second receiver 34 converts the second band received into a second electrical signal 36. The second band is chosen such that it lies within an electromagnetic absorption band of water and is also within an electromagnetic absorption band of carbon. Typically, this is at about 1.94 microns. The second electrical signal 36 is subtracted from a first electrical signal 26 by a computer 38. The result is determinitive of the amount of moisture in the paper material 12.

In general, the first source 18 and the second source 28 can be any source emitting the desired electromagnetic radiation. They can even be the same source, e.g., an infrared lamp. The dotted lines 20 and 30 can coincide and thus the first band and second band would impinge the same area on the paper material 12. In fact, for accuracy, this is preferred. In the event the dotted lines 20 and 30 coincide such that the first band and the second band impinge the same area on the paper material 12, then the dotted lines 22 and 32 would also coincide. In that event, the first receiver 24 and the second receiver 34 are positioned to receive both bands with a beam splitter such as that disclosed in U.S. Pat. No. 3,641,349. The first receiver 24 and the second receiver 34 can be any suitable detector, such as photodiode. The apparatus 10 of FIG. 1 uses the method of the present invention in which the measurement of the amount of moisture of the paper material 12 is accomplished by reflecting bands of electromagnetic radiation from the paper material 12. In this application, known as reflectance measurement, the calculation of the amount of moisture associated with the paper material 12 in the presence of carbon, by subtracting the second signal 36 from the first signal 26, can be further simplified to:

amount of moisture $= A + B(M + 1/M) - C(N + 1/N)$ where

A, B, C are constants of the apparatus 10 obtained from initial calibration;

M is the intensity of second band (1.94 micron) received without the paper material 12 (e.g., replace the paper material 12 by a reflector) divided by the intensity of the second band received with the paper material 12 (i.e., the intensity of second band received during the measurement process); and N is the intensity of the first band (1.8 micron) received without the paper material 12 (e.g., replace the paper material by a reflector) divided by the intensity of the first band received with the paper material 12 (i.e., the intensity of first band received during the measurement process).

The constants, A, B and C are determined from a collection of a plurality of paper material 12 having known values of moisture. The paper material 12 of this collection must have varying amounts (although not necessarily known amounts) of carbon. Each paper material 12 of this collection is placed in the apparatus 10 in the position shown in FIG. 1. For each paper material 12 of this collection, the values of M and N (as defined above) are determined. Using the method of Multiple Regression Analysis as taught by Philip R. Bevington in *Data Reduction and Error Analysis for the Physical Sciences* (McGraw-Hill Book Co, 1969), the constants A, B and C may be determined. While it is entirely possible to obtain the values of A, B, and C based upon a collection of three paper material 12 having known values of moisture and the measurements of M and N for each of those paper material 12, (the result would be three equations with three unknowns (A, B and C) and using simple algebra to solve for these unknowns), it is preferred to have a collection of a large number of paper material 12 having known values of moisture (typically ten or more), due to the statistical nature of measurement and the measuring process. The measurement of the intensity of the first band and the second band are made usually during standardization, i.e., when the apparatus 10 moves off-sheet from the paper material 12. These measurements are made to correct for errors caused by dirt build-up, source aging etc.

Referring to FIG. 2, there is shown a schematic side view of another apparatus 40 using the method of the present invention. A paper material 42, substantially in a sheet form, moves in a direction shown by arrow 44. The paper material 42 contains carbon particles 46 (greatly exaggerated). A first source 48 emits a first band of electromagnetic radiation, directed towards the paper material 42 in a direction along the dotted line 50. The first band, after impinging the paper material 42, transmits through it, and travels in the direction along the dotted line 52 and is received by a first receiver 54. The first receiver 54 converts the first band received into a first electrical signal 56. The first band is chosen such that it lies within an electromagnetic absorption band of carbon but lies outside of an electromagnetic absorption band of water. Typically, this is at about 1.8 microns. A second source 58 emits a second band of electromagnetic radiation, directed towards the paper material 42 in a direction along the dotted line 60. The second band, after impinging the paper material 42, transmits through it and travels in the direction along the dotted line 62 and is received by a second receiver 64. The second receiver 64 converts the second band received into a second electrical signal 66. The second band is chosen such that it lies within an electromagnetic absorption band of water and is also within an electromagnetic absorption band of carbon. Typically, this is at about 1.94 microns. The second electrical signal 66 is subtracted from a first electrical signal 56 by a computer 68. The result is determinitive of the amount of moisture in the paper material 42.

The apparatus 40 of FIG. 2 is similar to that disclosed and shown in U.S. Pat. No. 3,793,524. The apparatus 40 comprises a first diffusing plate 41 to one side of the paper material 42, while a second diffusing plate 43 is to the other side of the paper material 42. In addition, the sources 48, 58 and the receivers 54, 64 are off-set from one another; i.e., no amount of radiation is received directly by the receivers 54 and 64 from the sources 48 and 58. The advantages of the diffusing plates 41 and 43, and the off-set geometry are discussed fully in U.S. Pat. No. 3,793,524. In general, the first source 48 and the second source 58 can be any source emitting the desired electromagnetic radiation. They can even be the same source; e.g., an infrared lamp. The dotted lines 50 and 60 can coincide and thus the first band and second band would impinge the same area on the paper material 42. In fact, for accuracy, this is preferred. In the event the dotted lines 50 and 60 coincide such that the first band and the second band impinge the same area on the paper material 42, then the dotted lines 52 and 62 would also coincide. In that event, the first receiver 54 and the second receiver 64 are positioned to receive both bands with a beam splitter, such as that disclosed in U.S. Pat. No. 3,641,349. The first receiver 54 and the second receiver 64 can be any suitable detector such as photodiode. The apparatus 40 of FIG. 2 uses the method of the present invention in which the measurement of the amount of moisture of the paper material 42 is accomplished by transmitting bands of electromagnetic radiation through the paper material 42. In this application, known as transmittance measurement, the calculation of the amount of moisture associated with the paper material 42 in the presence of carbon, by subtracting the second signal 66 from the first signal 56, can be further simplified to:

$$\text{amount of moisture} = A + B\sqrt{M} - C\sqrt{N}$$

where
- A, B, C are constants of the apparatus 40 obtained from initial calibration;
- M is the intensity of the second band (1.94 micron) received without the paper material 42 (e.g., remove the paper material 42 and measure the intensity of the second band) divided by the intensity of the second band received with the paper material 42 (i.e., the intensity of the second band received during the measurement process); and
- N is the intensity of the first band (1.8 micron) received without the paper material 42 (e.g., remove the paper material 42 and measure the intensity of the second band) divided by the intensity of the first band received with the paper material 42 (i.e., the intensity of the first band received during the measurement process).

Similar to the previous discussion regarding the determination of the constants A, B and C for the method used by apparatus 10 of FIG. 1, the constants A, B and C of the method used by apparatus 40 is similarly determined from a collection of a plurality of paper material 42 having known values of moisture. The paper material 42 of this collection must have varying amounts (although not necessarily known amounts) of carbon. Each paper material 42 of this collection is placed in the apparatus 40 in the position shown in FIG. 2. For each paper material 42 of this collection, the values of M and N (as defined above) are determined. Using the method of Multiple Regression Analysis as previously discussed, the constants A, B and C may be determined. Due to the statistical nature of the measurement and measuring process, it is preferable to have a collection of a large number of paper material 42 having known values of moisture (typically ten or more). The measurements of the intensity of the first band and the second band are made usually during standardization, i.e., when the apparatus 40 moves off-sheet from the paper material 42. These measurements are made to correct for errors caused by dirt build-up, source aging, etc.

It should be appreciated that the method of the present invention is not limited in its application to the determination of the amount of moisture associated with paper material in the presence of carbon, either through reflectance measurement or transmittance measurement. The method of the present invention can be used to determine the amount of any substance associated with a material in the presence of a contaminant. For example, the method of the present invention can also be used to determine the amount of plastic in a plastic film in the presence of carbon, or to determine the amount of water in a paper material in the presence of other color dyes.

The theoretical basis for the method of the present invention is as follows: The amount of monochromatic light reflected or transmitted from a diffusing sheet depends on the absorption coefficient K and the scattering coefficient S. It shall be assumed that, in accordance with Beer's Law, the absorption depends on the concentration of substance in the sheet, the concentration of contaminant, and the concentration of some unknown (albeit small amount). In addition, it is assumed that the absorption coefficients are additive so that the total absorption coefficient K is the sum:

$$K = K(\text{substance}) + K(\text{contaminant}) + K(\text{other}) = K_S + K_C + K_O$$

From the theory of Kubelka and Munk (Kubelka, Paul, "New Contributions to the Optics of Intensely Light-Scattering Materials, Part I," Journ. Opt. Soc. Am., 38, 1945.), the total absorption coefficient can also be related to reflectance R and scattering coefficient S. Thus:

$$K_M = K_{MS} + K_{MC} + K_{MO} = \frac{S_M}{2}\left(M + \frac{1}{M}\right) - S_M$$

$$K_N = K_{NS} + K_{NC} + K_{NO} = \frac{S_N}{2}\left(N + \frac{1}{N}\right) - S_N$$

where M and N are the ratio of measure and reference bands respectively, as previously discussed. If it is assumed that the contaminant absorbs equally at the reference channel and at the measure channel, i.e., $K_{MC} = K_{NC}$ then the difference of the two equations yields:

$$(K_{MS} - K_{NS}) + (K_{MO} - K_{NO}) =$$

-continued $$\frac{S_M}{2}\left(M + \frac{1}{M}\right) - \frac{S_N}{2}\left(N + \frac{1}{N}\right) - (S_M - S_N)$$

since $(K_{MS} - K_{NS})$ is proportional to the amount of substance, and the terms $(K_{MO} - K_{NO})$, $S_M/2$, $S_N/2$ and $(S_M - S_N)$ are constants, the equation becomes:

$$\text{amount of substance} = A + B\left(M + \frac{1}{M}\right) - C\left(N + \frac{1}{N}\right)$$

where A, B and C are constants determined by calibration, as previously discussed. In the case of light transmitted through the sheet, the effect of the light scattered from the sheet *and* then reflected from the diffusing plates to impinge the sheet, must be considered. Thus, the theory of Kubelka and Munk must be rewritten to include multiple passes and to take into account the off-set geometry. The analysis, thereafter, however, is the same. The coefficient of absorption K can be determined for the measured channel and the reference channel. The difference is taken and the resultant is proportional to the amount of substance.

It should be appreciated that the method of the present invention does not require a large amount of a priori data. Moreover, because it does not use the ratio of the signal of the reference channel to the measure channel to determine the moisture content of the paper material, as taught by the prior art, it is accurate and has a wide range of applicability to correct for the presence of any contaminant, including carbon in paper.

What is claimed is:

1. A method of measuring the amount of a substance associated with a sheet material in the presence of a contaminant, said contaminant having an electro-magnetic radiation absorption characteristic different from the electro-magnetic radiation absorption characteristic of said substance, wherein said method comprises the steps of:

emitting a first band of electro-magnetic radiation, wherein said first band lies outside an absorption band of said substance, and lies within an absorption band of said contaminant;

directing said first band to impinge said material;

detecting said first band after reflecting from said material;

generating a first signal, in response to said first band detected;

generating a second signal corresponding to the intensity of the first band detected without material;

emanating a second band of electromagnetic radiation, wherein said second band lies within an absorption band of said substance, and also lies within an absorption band of said contaminant;

directing said second band to impinge said material;

receiving said second band after reflecting from said material;

generating a third signal, in response to said second band received;

generating a fourth signal corresponding to the intensity of the second band received without material; and calculating the amount of substance in accordance with the formula:

$$\text{amount of substance} = A + B(M + 1/M) - C(N + 1/N)$$

where

A, B, C are calibration constants;

M = intensity of second band received without material divided by intensity of second band received with material;

N = intensity of first band detected without material divided by intensity of first band detected with material.

2. A method of measuring the amount of a substance associated with a sheet material in the presence of a contaminant, said contaminant having an electro-magnetic radiation absorption characteristic different from the electromagnetic radiation absorption characteristic of said substance, wherein said method comprises the steps of:

emitting a first band of electro-magnetic radiation, wherein said first band lies outside an absorption band of said substance, and lies within an absorption band of said contaminant;

directing said first band to impinge said material;

detecting said first band after transmitting through said material;

generating a first signal, in response to said first band detected;

generating a second signal corresponding to the intensity of the first band detected without material;

emanating a second band of electromagnetic radiation, wherein said second band lies within an absorption band of said substance, and also lies within an absorption band of said contaminant;

directing said second band to impinge said material;

receiving said second band after transmitting through said material;

generating a third signal, in response to said second band received;

generating a fourth signal corresponding to the intensity of the second band received without material; and calculating the amount of substance in accordance with the formula:

$$\text{amount of substance} = A + B\sqrt{M} - C\sqrt{N}$$

where

A, B, C are calibration constants;

M = intensity of second band received without material divided by intensity of second band received with material;

N = intensity of first band detected without material divided by intensity of first band detected with material.

3. A method of measuring the amount of water associated with a paper material in the presence of carbon, wherein said method comprises the steps of:

emitting a first band of electromagnetic radiation, wherein said first band lies outside the electromagnetic absorption band of water but lies within the electromagnetic absorption band of carbon;

directing said first band to impinge said paper material;

detecting said first band after reflecting from said paper material;

generating a first signal, in response to said first band detected;

generating a second signal corresponding to the intensity of the first band detected without material;
emanating a second band of electromagnetic radiation, wherein said second band lies within the electromagnetic absorption band of water and lies within the electromagnetic absorption band of carbon;
directing said second band to impinge said paper material;
receiving said second band after reflecting from said paper material;
generating a third signal, in response to said second band received;
generating a fourth signal corresponding to the intensity of the second band received without material; and
calculating the amount of water in accordance with the formula:

$$\text{moisture} = A + B(M + 1/M) - C(N + 1/N)$$

where
A, B, C are calibration constants;
M = intensity of second band received without material divided by intensity of second band received with material;
N = intensity of first band detected without material divided by intensity of first band detected with material.

4. The method of claim 3 wherein said first band of electromagnetic radiation lies at about 1.8 microns.

5. The method of claim 4 wherein said second band of electromagnetic radiation lies at about 1.94 microns.

6. A method of measuring the amount of water associated with a paper material in the presence of carbon, wherein said method comprises the steps of:
emitting a first band of electromagnetic radiation, wherein said first band lies outside the electromagnetic absorption band of water but lies within the electromagnetic absorption band of carbon;
directing said first band to impinge said paper material;
detecting said first band after transmitting through said paper material;
generating a first signal, in response to said first band detected;
generating a second signal corresponding to the intensity of the first band detected without material;
emanating a second band of electromagnetic radiation, wherein said second band lies within the electromagnetic absorption band of water and lies within the electromagnetic absorption band of carbon;
directing said second band to impinge said paper material;
receiving said second band after transmitting through said paper material;
generating a third signal, in response to said second band received;
generating a fourth signal corresponding to the intensity of the second band received without material; and
calculating the amount of water in accordance with the formula:

$$\text{moisture} = A + B\sqrt{M - C}\sqrt{N}$$

where
A, B, C are calibration constants;
M = intensity of second band received without material divided by intensity of second band received with material;
N = intensity of first band detected without material divided by intensity of first band detected with material.

7. The method of claim 6 wherein said first band of electromagnetic radiation lies at about 1.8 microns.

8. The method of claim 7 wherein said second band of electromagnetic radiation lies at about 1.94 microns.

* * * * *